United States Patent [19]

Laufenberg et al.

[11] Patent Number: 5,324,847

[45] Date of Patent: Jun. 28, 1994

[54] OLEFINICALLY UNSATURATED ADDUCTS OF ETHYLENE WITH POLYUNSATURATED FATTY ACIDS OF FATTY ACID ESTERS, A PROCESS FOR THEIR PRODUCTION AND THEIR USE

[75] Inventors: Alfred Laufenberg, Dormagen; Arno Behr, Duesseldorf, both of Fed. Rep. of Germany

[73] Assignee: Henkel Kommanditgesellschaft auf Aktien, Duesseldorf, Fed. Rep. of Germany

[21] Appl. No.: 915,696

[22] PCT Filed: Jan. 15, 1991

[86] PCT No.: PCT/EP91/00054

§ 371 Date: Jul. 24, 1992

§ 102(e) Date: Jul. 24, 1992

[87] PCT Pub. No.: WO91/11428

PCT Pub. Date: Aug. 8, 1991

[30] Foreign Application Priority Data

Jan. 24, 1990 [DE]  Fed. Rep. of Germany ....... 4002012

[51] Int. Cl.$^5$ .................................................. C11C 3/06
[52] U.S. Cl. .................................... 554/162; 554/163
[58] Field of Search ................. 554/163, 165, 162

[56] References Cited

U.S. PATENT DOCUMENTS

| | | | |
|---|---|---|---|
| 3,636,122 | 1/1972 | Cramer et al. | 260/680 |
| 3,734,859 | 5/1973 | Ward | 252/108 |
| 3,753,968 | 8/1973 | Ward | 260/97.6 |
| 3,966,798 | 6/1976 | Intille et al. | 260/486 |
| 4,318,860 | 3/1982 | Hsu et al. | 554/162 |
| 4,371,469 | 2/1983 | Foglia et al. | 554/161 |
| 4,973,431 | 11/1990 | Struve et al. | 554/141 |

FOREIGN PATENT DOCUMENTS

| | | |
|---|---|---|
| 10807 | 1/1983 | European Pat. Off. . |
| 206367 | 4/1986 | European Pat. Off. . |
| 0206367 | 12/1986 | European Pat. Off. . |
| 2016133 | 12/1970 | Fed. Rep. of Germany . |
| 2253930 | 5/1974 | Fed. Rep. of Germany . |

OTHER PUBLICATIONS

Radical Addition of Methyl Acetoxy Acetate to Olefins and Pyrolysis of the Adducts Feb., 1967.
Fat Sci. Tech. 1, 1 (1988).
J. O. Metzger et al., Fat Sci. Technol., 1, (1989), p. 18.
A. Smith et al., Biomed. Mass Spectrom, 6 (8), pp. 347-349 1979.
M. Bochmann et al., Journal of Molecular Catalyst, 22 (1984), pp. 363-365.
G. Wilkinson (Ed.), Comprehensive Organometallic Chemistry, (1982), pp. 414-429.

Primary Examiner—José G. Dees
Assistant Examiner—Samuel Barts
Attorney, Agent, or Firm—Wayne C. Jaeschke; John E. Drach; Henry E. Millson, Jr.

[57] ABSTRACT

Olefinically unsaturated adducts of ethylene on polyunsaturated fatty acids with 18 to 22 carbon atoms or on esters of these fatty acids with $C_1$-$C_{36}$ alkanols in molar ratios of ethylene to fatty acids or fatty acid esters in the range from 1:1 to 3:1 obtainable by reacting the fatty acids or fatty acid esters with ethylene at elevated temperature and pressure in the presence of compounds of the transition metals Ru, Rh, Pd, Ir and Pt as catalysts to form an olefinically unsaturated adduct.

6 Claims, No Drawings

OLEFINICALLY UNSATURATED ADDUCTS OF ETHYLENE WITH POLYUNSATURATED FATTY ACIDS OF FATTY ACID ESTERS, A PROCESS FOR THEIR PRODUCTION AND THEIR USE

BACKGROUND OF THE INVENTION

1. Field of the Invention

This invention relates to olefinically unsaturated adducts of ethylene with polyunsaturated $C_{18-22}$ fatty acids or esters thereof with $C_{1-36}$ alkanols in molar ratios of ethylene to the fatty acids or fatty acid esters of 1:1 to 3:1 obtainable by reaction of the fatty acids or fatty acid esters with ethylene at elevated temperature and elevated pressure in the presence of compounds of transition metals from the group consisting of Ru, Rh, Pd, Ir and Pt as catalysts.

2. Statement of Related Art

Fatty acids branched in the alkyl chain of the Guerbet acid type, obtainable by "guerbetization" of the corresponding fatty alcohols and oxidation of the Guerbet alcohols to the corresponding acids, are technologically interesting intermediate products because they, or their alkyl esters, have distinctly reduced pour points comparison with the corresponding unbranched isomers. However, the production of Guerbet acids is technologically complicated and can only be carried out with unsatisfactory yields. Accordingly, there has been no shortage of attempts to produce corresponding fatty acid derivatives branched in the alkyl chain from fatty acids of esters thereof. A typical example of this is the layer-silicate-catalyzed dimerization of fatty acids. Unfortunately, considerable quantities of tirmeric fatty acids and methyl-branched fatty acids, so-called isofatty acids, are also formed in this reaction. Another, albeit complicated, process gives branched fatty acid derivatives from conjuene fatty acids in the trans-trans form with activated dienophiles under the conditions of a Diels-Alder reaction; for example, a branched $C_{21}$ dicarboxylic acid can be obtained in this way from linoleic acid and acrylic acid, cf. U.S. Pat. Nos. 3,734,859, and 3,753,968, DE-B 2 253 930. Other branched fatty acid derivatives have been obtained by thermal or acid-catalyzed addition of activated enophiles onto unsaturated fatty acid derivatives. For example, maleic anhydride can be added onto oleic acid in the presence of an acid as catalyst in yields of up to 70%, of. Fat. Sci. Technol., 1, 1 (1988). However, the presence of more than one carboxyl group in the reaction products mentioned above has often proved to be troublesome.

Finally, attempts have also been made to add saturated hydrocarbons onto fatty acids by heat-initiated radical addition of saturated hydrocarbons onto fatty acids. The addition of cyclohexane onto oleic acid methyl ester at 340° C./200 bar gives alkyl-branched fatty acids with 70% selectivity, but in a yield of only 2.8%, of. J.O. Metzget et al., Fat. Sci. Technol. 1 (1989), 18.

DESCRIPTION OF THE INVENTION

The present invention is directed to the provision of olefinically unsaturated adducts of ethylene with polyunsaturated fatty acids of the type mentioned at the beginning which can be readily obtained in high yields. The compounds provided in accordance with the invention are new products which, for example, differ in their chain length alone from the naturally occurring ethyl-branched fatty acids containing a total of 12 to 18 carbon atoms described in A. Smith etal. Biomed. Mass Spectrom., 6 (8), 347–349.

Suitable starting products for the production of the olefinically unsaturated adducts according to the invention are unsaturated fatty acids containing 18 to 22 carbon atoms and more than one olefinic double bond, such as linoleic acid, isomerized linoleic acid containing conjugated double bonds (so-called $C_{18}$:2-conjuene fatty acid), linolenic acid, arachidonic acid, docosadienoic acid, docosahexaenoic and eicosapentaenoic acid, which can be obtained in the form of technical mixtures with other fatty acids from renewable natural raw materials, for example from sunflower oil, tall oil or fish oil. As usual in oleochemistry, these polyunsaturated fatty acids are generally not used in the form of their pure compounds, but rather in the form of technical mixtures for the preparation of the adducts according to the invention. The above-mentioned fatty acids are preferably used not only as such, but also in the form of their esters with $C_{1-36}$ alkanols, more particularly with $C_{1-4}$ alkanols. Typical examples of such alkanols for the formation of esters with the fatty acids mentioned above are methanol, ethanol, propanol, butanol, pentanol, hexanol, octanol, decanol, dodecanol, tetradecanol, hexadecanol, octadecanol and higher fatty alcohols or fatty alcohol derivatives containing up to 36 carbon atoms, for example $C_{36}$ Guerbet alcohols.

According to the invention, the polyunsaturated fatty acids or fatty acid esters mentioned above are added onto ethylene at elevated temperature and pressure in the presence of compounds of transition metals from the group consisting of Ru, Rh, Pd, Ir and Pt.

The following are typical examples of catalysts suitable for use in accordance with the invention:

$RhCl_3.3H_2O$
$RhBr_3.3H_2O$
$[(C_2H_4)_2RhCl]_2$
$Rh(NO_3)_3.2H_2O$
$Rh(OOCCH_3)_2.2H_2O$
$Rh(acetylacetonate)_3$
$RhF_3.6H_2O$
$RhI_3$
$Rh(CN)_3.3H_2O$
$Rh_2(SO_4)_3$
$Rh_2(CO_3)_3$
$[(1.5-cyclooctadiene)RhCl]_2$
$[(C_2H_4)_2Rh(acetylacetonate)]$
$[(1.3-butadiene)RhCl]_2$ cyclopentadienyl-olefin complexes, such as $[(n-C_5H_5)Rh-(C_2H_4)_2]$.

Where the catalysts suitable for use in accordance with the invention are present in anhydrous form, it may be advisable to add a small quantity of water to the reaction mixture.

The catalysts suitable for use in accordance with the invention are known as such for the addition of ethylene onto alkadienes, cf. U.S. Pat. No. 3,636,122; M. Bochmann et al., Journal of Molecular Catalysis, 22 (1984), 363–365; G. Wilkinson (Ed.), Comprehensive Organometallic Chemistry, pages 414–429, Pergamon Press (1982); A.C.L. Su, Advances in Organometallic Chemistry, Vol. 17, pages 271–283. However, these publications, to the subject matter of which reference is hereby specifically made, are not concerned with the addition of alkenes onto fatty acids or fatty acid derivatives or other fatty compounds.

Other catalysts suitable for use in accordance with the invention are, for example, PdCl$_2$
PtCl$_2$
IrCl$_3$
OsCl$_3$
Ru(acetylacetonate)$_3$.

Mixtures of 1:1, 2:1 and 3:1 adducts of ethylene with the fatty acids or fatty acid esters are generally formed with the catalysts suitable for use in accordance with the invention. However, the percentage contents of the various adducts can be varied by modifying the reaction conditions, such as pressure, temperature and reaction time. However, if suitable phosphine or phosphite ligands, for example

P(C$_4$H$_9$)$_3$
P(OC$_4$H$_9$)$_3$
P(C$_6$H$_5$)$_3$
P(OC$_6$H$_5$)$_3$ or other ligands known from the prior art just discussed and from DE-B 20 16 133, are added to the reaction mixture in addition to the catalysts, the composition of the adduct mixtures may be selectively influenced. Thus, in the case of reaction systems which mainly give 2:1 adducts without such ligands, 3:1 adducts are mainly formed where large ligands are used while 1:1 adducts are mainly formed where small ligands are used. Similar effects can be obtained to an extent by addition to the reaction system of promoters such as LiCl, FeCl$_3$ or AgBF$_4$ which are also known as such from the last-mentioned prior art.

The structure of the olefinically unsaturated adducts according to the invention is not uniform. In the case of linoleic acid (or the C$_{18}$ conjuene fatty acid derived therefrom), it could be shown that the addition of the first ethylene molecule takes place between the 9 and 12 positions of the carbon chain of the linoleic acid, the 1:1 adduct having the same number of double bonds as the fatty acid used as starting material. However, the position of the double bonds is uncertain. In no case are the double bonds further than 4 carbon atoms from the branching and, basically, they are in the α, δ- or α,γ-position to one another. The second and, optionally, the third ethylene molecule is then added onto a double bond situated in the branching. It may be assumed that at least some of the adducts obtained in accordance with the invention have one of the structures shown on the following page:

In one advantageous embodiment of the invention, the polyunsaturated fatty acids optionally used in the form of their esters contain 2 to 5 and, more particularly, from 2 to 3 olefinic double bonds.

In another advantageous embodiment of the invention, the adducts are obtained under an ethylene pressure in the range from 5 to 60 bar and at a temperature in the range from 50° to 140° C. the reaction optionally being carried out in the presence of inert organic solvents, such as hexane, chloroform or the like.

In another advantageous embodiment of the invention, the catalysts are used in a quantity of 0.02 to 2 mol-%, based on fatty acids or fatty acid esters.

Rhodium compounds are advantageously used as the catalysts, rhodium compounds from the group consisting of RhCl$_3$ and RhBr$_3$ (including hydrates thereof) and [(C$_2$H$_4$)$_2$-RhCl]$_2$ preferably being used as catalysts.

The invention also relates to a process for the production of olefinically unsaturated adducts of ethylene with polyunsaturated fatty acids containing 18 to 22 carbon atoms or esters thereof with C$_{1-36}$ alkanols in molar ratios of ethylene to the fatty acids or fatty acid esters of 1:1 to 3:1 having the features described above.

The olefinically unsaturated adducts according to the invention are suitable as starting products for the production of saturated, branched fatty acids containing 20 to 28 carbon atoms or esters thereof with C$_{1-36}$ alkanols which may be used, for example, as lubricant additives or in cosmetic formulations.

The invention is illustrated by the following Examples.

Example 1

8.2 g of a technical fatty acid mixture containing 56% by weight conjugated C$_{18}$:2 fatty acid were reacted with 100 mg RhCl$_3$.3H$_2$O in 10 ml hexane for 20 h at 100° C./30 bar cold ethylene pressure in a 75 ml steel autoclave. 63.1% ethylene adducts, based on conjuene fatty acid, were obtained (as determined by gas chromatography), being made up of 34.9% 1:1 adduct, 44.2% 2:1 adduct and 20.9% 3:1 adduct.

Example 2

2.5 kg of a technical conjuene fatty acid according to Example 1, 0.8 g RhCl$_3$.3H$_2$O and 1 l hexane were reacted for 20 h at 100° C./20 bar constant ethylene

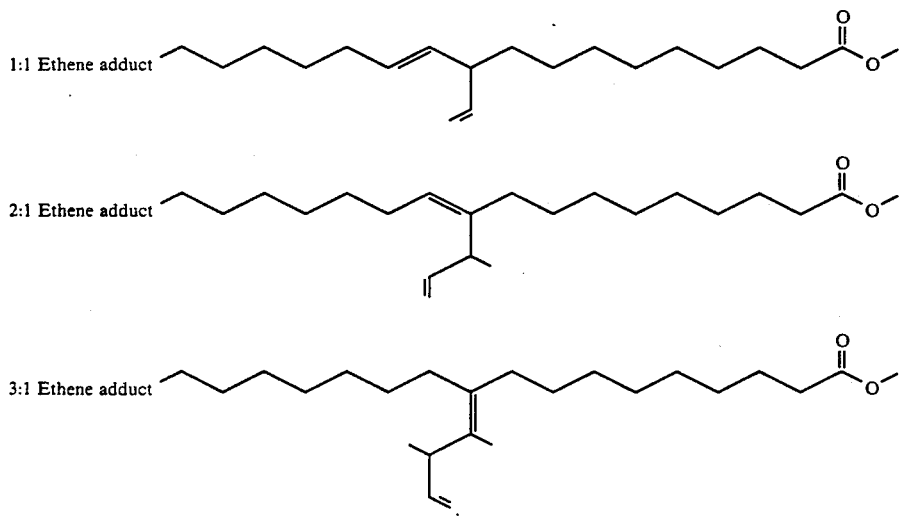

pressure in a 5 liter stirred autoclave equipped with a turbine stirrer. Ethylene adducts were obtained in a yield of 89.4%, being made up of 23.7% 1:1 adduct, 41.7% 2:1 adduct and 34.6% 3:1 adduct.

Example 3

8.2 g of a technical linoleic acid methyl ester ( 67.8% methyl linoleate, 22.4% methyl oleate) and 100 mg $RhCl_3.3H_2O$ were reacted with 10 ml chloroform at 100° C. under a cold ethylene pressure of 20 bar. The adduct yield, based on methyl linoleate, was 57.8%, the adducts being made up of 30.8% 1:1 adduct, 42.0% 2:1 adduct and 27.2% 3:1 adduct.

Example 4

The repetition of Example 3 under a cold ethylene pressure of 30 bar produced an adduct yield of 57.6%, the adducts being made up of 31.5% 1:1 adduct, 52.2% 2:2 adduct and 16.3 % 3:1 adduct.

Example 5

8.2 g of a technical $C_{18}:2$ conjuene methyl ester (containing 60.3% conjuene ester, 6.2% linoleic acid methyl ester and 24.4% oleic acid methyl ester) in 10 ml chloroform were reacted at 100° C./20 bar cold ethylene pressure. Ethylene adducts were obtained in a yield of 93.5%, the adducts being made up of 27.5% 1:1 adduct, 51.1% 2:1 adduct and 21.4 % 3:1 adduct.

Example 6

The repetition of Example 5 under a cold ethylene pressure of 30 bar produced a total yield of ethylene adducts of 88.5%, the adducts being made up of 36.5% 1:1 adduct, 51.0% 2:1 adduct and 12.1% 3:1 adduct.

Example 7

The repetition of Example 6 in the presence of 185.1 mg $FeCl_3$ as promoter produced a total adduct yield of 81.8%, the adducts being made up of 22.8% 1:1 adduct, 46.9% 2:1 adduct and 30.3% 3:1 adduct.

Example 8

The repetition of Example 6 with hexane instead of chloroform produced a total adduct yield of 87.4%, the adducts being made up of 24.8% 1:1 adduct, 59.7% 2:1 adduct and 15.5% 3:1 adduct.

Example 9

The repetition of Example 6 with 74 mg $[(C_2H_5)_2RhCl]_2$ instead of $RhCl_3.3H_2O$ produced a total adduct yield of 78.0%, the adducts being made up of 24.2% 1:1 adduct, 61.8% 2:1 adduct and 13.0% 3:1 adduct. The total yield rose to 86.5% when 86.4 mg $P(C_4H_9)_3$ was added to the reaction mixture.

Example 10

The repetition of Example 6 using 13 mg $RhBr_3.3H_2O$ instead of $RhCl_3.3H_2O$ in the absence of a solvent produced a total yield of ethylene adducts, based on the conjuene ester content, of 94.6%, the adducts being made up of 17.7% 1:1 adduct, 62.8% 2:1 adduct and 16.5% 3:1 adduct.

Example 11

Influence of phosphine and phosphite ligands

Example 3 was repeated with addition of 76.76 g (9.380 mmol) $P(C_4H_9)_3$. The total adduct yield was 54.5%, based on . methyl linoleate, the adducts being made up of 32.4% 1:1 adduct, 16.2% 2:1 adduct and 6.0% 3:1 adduct.

Repetition with 9.50 mg (0.038 nunol) $P(OC_4H_9)_3$ produced a total adduct yield of 57.8%, the adducts being made up of 34.9% 1:1 adduct, 16.4% 2:1 adduct and 6.5% 3:1 adduct.

Repetition with 9.96 mg( 0.038 mmol) $P(C_6H_5)_3$ produced a total adduct yield of 64.2%, the adducts being made up of 8.7% 1:1 adduct, 17.9% 2:1 adduct and 37.5% 3:1 adduct.

Repetition with 117.8 mg (0.38 mmol) $P(OC_6H_5)_3$ produced a total adduct yield of 59.2% for an adduct distribution similar to that obtained with $P(C_6H_5)_3$.

Example 12

Example 8 was repeated with various catalysts instead of the catalyst described there. The quantities of catalyst used (0.38 mmol in each case), the type of catalyst used and the adduct yields (based in each case on conjuene ester) are shown below:

| Catalyst | Adduct yield |
| --- | --- |
| 123.5 mg $Rh(NO_3)_3.2H_2O$ | 17.6% |
| 90.8 mg (0.19 mmol) $[Rh(OAc)_2].2H_2O$ | 46.6% |
| 161.1 mg $Rh(acac)_3$ + 2.0 µl $H_2O$ | 44.1% |
| 151.4 mg $Ru(acac)_3$ + 2.0 µl $H_2O$ | 17.3% |
| 67.4 mg $PdCl_2$ | 14.8% |
| 101.1 mg $PtCl_2$ | 32.3% |
| 113.5 mg $IrCl_3$ + 2.0 µl $H_2O$ | 13.6% |
| 112.7 mg $OsCl_3$ + 2.0 µl $H_2O$ | 20.3% |

Only 1:1 adducts were formed.

Example 13

A $C_{36}$ Guerbet ester of a technical $C_{18}:2$ conjuene fatty acid (17.5 g) having the composition shown in Example 1 was reacted with ethylene under the same conditions as in that Example in the presence of 100 mg $RhCl_3.3H_2O$ and 10 ml hexane. The total adduct yield was 52.4%, based on conjuene ester, the adducts being made of 16.4% 1:1 adduct, 27.0% 2:1 adduct and 9.2% 3:1 adduct.

What is claimed is:

1. Olefinically unsaturated adducts of ethylene with polyunsaturated $C_{18-22}$ fatty acids or esters thereof esterified with $C_{1-36}$ alkanols produced by the process comprising reacting unsaturated fatty acids containing 18 to 22 carbon atoms and more than one olefinic bond or esters thereof esterified with $C_{1-36}$ alkanols with ethylene at a temperature of from about 50° C. to about 140° C. and at a pressure of from about 5 to about 60 bar in the presence of transition metal compounds selected from the group consisting of Ru, Rh, Pd, Ir, or Pt wherein the molar ratio of ethylene to fatty acid or fatty acid ester is from about 1:1 to about 3:1 to form an olefinically unsaturated adduct.

2. The olefinically unsaturated adducts as claimed in claim 1 wherein said fatty acids containing 18 to 22 carbon atoms also contain from 2 to 5 olefinic bonds.

3. The olefinically unsaturated adducts as claimed in claim 2 wherein said fatty acids containing 18 to 22 carbon atoms also contain from 2 to 3 olefinic bonds.

4. The olefinically unsaturated adducts as claimed in claim 1 wherein the amount of said transition metal compound is from about 0.02 to about 2 mole % based on fatty acid or fatty acid ester.

5. The olefinically unsaturated adducts as claimed in claim 1 wherein said transition metal compound is a rhodium compound.

6. The olefinically unsaturated adducts as claimed in claim 5 wherein said rhodium compound is $RhCl_3$, $RhBr_3$, hydrates of $RhCl_3$, $RhBr_3$, or $((C_2H_4)_2RhCl)_2$.

* * * * *